(12) United States Patent
Niggebrugge

(10) Patent No.: US 8,099,244 B2
(45) Date of Patent: Jan. 17, 2012

(54) METHOD, A COMPUTER PROGRAM AND A COMPUTER SYSTEM FOR DETERMINATION WHETHER A SUBJECT HAS AN INCREASED RISK FOR ACQUIRING A DISEASE

(75) Inventor: Arthur H. P. Niggebrugge, Leiden (NL)

(73) Assignee: Stichting Novo Health, Den Haag (NL)

( * ) Notice: Subject to any disclaimer, the term of this patent is extended or adjusted under 35 U.S.C. 154(b) by 542 days.

(21) Appl. No.: 12/270,694

(22) Filed: Nov. 13, 2008

(65) Prior Publication Data
US 2009/0177405 A1 Jul. 9, 2009

(30) Foreign Application Priority Data
Nov. 13, 2007 (EP) ..................................... 07120592

(51) Int. Cl.
*G06F 19/00* (2011.01)
(52) U.S. Cl. ......................................................... 702/19
(58) Field of Classification Search ...................... 702/19
See application file for complete search history.

(56) References Cited

OTHER PUBLICATIONS

Kurt Schweigman, Cardiovascular Disease Risk Factor Wareness in American Indian Communities: The Strong Heart Study, Ethnicity & Disease, vol. 16, Summer 2006, p. 647-652.*

* cited by examiner

*Primary Examiner* — Tung S Lau
(74) *Attorney, Agent, or Firm* — Leydig, Voit & Mayer Ltd.

(57) ABSTRACT

A method, a computer program and a computer system are described for determining whether a subject has an increased risk for acquiring a disease, said method comprising selecting at least one disease, for example using a user interface wherein in a field 23a suitable plurality of diseases is provided. In field 23b, an interactive window for the user is provided for posing questions and for acquiring answers. The questions are preferably generated by a question generation engine and are projected in the field 26. Answers, provided by the user are acquired using the same interactive field 26 after which they are processed together with deterministically established partial risk factors linked to said answers leading to a computation of a total risk factor of the user for the selected disease. In field 23c a number of tests which may be recommended for a suitable screening procedure is presented.

15 Claims, 4 Drawing Sheets

METHOD, A COMPUTER PROGRAM AND A COMPUTER SYSTEM FOR DETERMINATION WHETHER A SUBJECT HAS AN INCREASED RISK FOR ACQUIRING A DISEASE

CROSS-REFERENCE TO RELATED APPLICATION

This application claims the priority benefit of Niggebrugge, European Patent Application No. EP 07120592, filed on Nov. 13, 2007, and entitled "A Method, A Computer Program And A Computer System For Determination Whether A Subject Has An Increased Risk For Acquiring A Disease" the contents of which are incorporated herein by reference in its entirety, including any references therein.

FIELD OF THE INVENTION

The invention relates to a method, a computer-readable medium including computer-executable instructions in the form of a computer program, and a computer system including a computer-readable medium including a computer-readable medium including computer-executable instructions for determination of whether a subject has an increased risk for acquiring a disease.

BACKGROUND OF THE INVENTION

It is acknowledged that a purposeful screening for diagnosing a certain disease may have a positive impact on a cumulative health improvement for a certain group within a population. Screening is defined as a systematic application of a test or a suitable investigation for purposes of determination whether a subject in question had acquired a disease while symptoms of such disease are not present.

It has been understood that there is a trade-off between potential integral health improvement for the group within the population, expressed, for example, as a decrease in an integral mortality rate or a decrease in morbidity for said group and a potential damage to the certain group caused by triggering awareness of a fact that a subject from that group may be affected by a disease. Such damage may be related to a psychological anxiety of subjects subjected to screening procedures. Next to this, it is a common approach for many national health management policies that prophylactic screening may only be allowed when expected integral potential health improvement for at least the certain group within the population is greater than expected health hazard due to subjecting said group to screening.

Currently, general practitioners act as a primary filtering stage by trying to ascertain for which patients screening is advantageous and for which patients it is not. This is often done by subjecting a patient to a questionnaire and by making an educated guess regarding a risk factor of the patient under consideration with respect to a certain disease. It will be that although this practice is not yet actual, but in cases when a person desires to be screened for a plurality of diseases, he would first address his general practitioner. A filtering task for finding out whether this person will indeed be helped by such screening, posed before the general practitioner, is almost impossible to accomplish, as he or she has to spend hours interrogating the person in question. Such situation is undesirable, cost ineffective and may be inaccurate due to the fact that it is prone to human judgment errors.

SUMMARY OF THE INVENTION

It is an object of the invention to provide a method of determination whether a subject has an increases risk for acquiring a certain disease, which is accurate and reliable. To this end the method according to the invention comprises the steps of:
selecting at least one disease;
interactively subjecting the subject to a plurality of questions relevant for the at least one disease;
acquiring respective answers from the subject to the said plurality of questions;
computing a risk factor for the subject for the at least one disease using said answers and an accessible database comprising a plurality of respective deterministically established partial risk factors for diseases, said partial risk factors being assigned to the said acquired answers.

At least the above-described computing step is performed, in the disclosed embodiment, by a computer system comprising a computer-readable medium including computer-executable instructions for carrying out the recited functionality It has been found to be advantageous to provide means of quantitative assertion of a risk factor for a disease under consideration based on established deterministic medical knowledge. Such deterministic risk factors are per se known and may be subject of one or more national or supra-national health management programs. For example, in The Netherlands, a Central Authority on Population Investigations has published a directive comprising deterministic risk factors influencing integral risk on acquiring osteoporosis. Such risk factor is assigned with a respective score, whereby in cases when the patient is marked with at least 4 points, a specific screening program is suggested to that patient. For patients diagnosed with osteoporosis based on suggested screening investigations which were subsequently treated for this disease it is established that a decrease of chance of (new) fracturing may be as high as about 69%. Although any person, notably any woman may request a screening against osteoporosis, any mass screening of a not pre-selected group will not yield any integral improvement of the health for the population. Next to this such mass screening is extremely costly and poses high financial loads on health insurers.

In another example, see A. P. M. Boll "Screening for abdominal aortal aneurysms: single centre randomized controlled trial, BMJ 330; 2005", it is shown that a mortality rate of 2-3% of Dutch male population aged 60 and more due to aortal rupture may be decreased by 50% by carrying out a suitable timely diagnostic step, for example an ultrasonic examination of the abdomen. It is therefore, important to select a group of potential patients within the overall male population, to carefully identify individuals having increased risk for having an aortal aneurysm and to subject the individuals to timely screening investigations.

It is further understood that a core group for which screening has a net positive effect resulting in a net increase of life expectation for the entire population may be identified based on a quantitative analysis of risk factors of an individual for any disease based on clinically relevant, deterministic risk factors assigned for that disease. Such risk factors are published, for example in "Central Bureau voor de Statistiek (CBS). Gezondheid en Welzijn. Voorburg/Heerlen; 2007", which may be found on http://www.cbs.nl/nl_NL/menu/themas/gezondheid-welzijn/cijfers/default.htm. A further source of deterministic risk factors is "Prisman cijfers. Classificatie van ziekten systematisch deel 1 en classificatie van ziekten alfabetisch deel 2; 2003". A still further source of deterministic risk factors comprises "Kwaliteitsinstituut voor de gezondheidszorg CBO. Richtlijnen; 2007", which may be found on http://www.cbo.nl/product/richtlijnen/folder20021023121843/default_view. A still further source of deterministic factors comprises "National Institute for Health and Clinical Excellence (NICE). Published clinical guidelines; 2007", which may be found on http://www.nice.org.uk/page.aspx?o=guidelines.completed. It will be appreciated that finding sources of data related to clinically acknowledged deterministic risk factors for a selected disease lies within reach of the person skilled in the art.

Preferably, a disease is selectable from the following non-exhaustive list of diseases for which deterministic risk factors are known:
- alcohol abuse;
- aneurysma aortae abdominalis;
- cerebral vascular accident;
- cervix cancer;
- chlamydia;
- increased cholesterol level;
- colon cancer;
- COPD;
- coronary dysfunction;
- dementia;
- depression;
- diabetes mellitus;
- diabetic nephropathy;
- diabetic retinopathy;
- erectile dysfunction;
- hearing dysfunction;
- glaucoma;
- HIV/AIDS;
- hypertension;
- thyroid dysfunction;
- lung cancer;
- breast cancer;
- melanoma;
- miction dysfunction;
- cancer of oral cavity;
- renal disease;
- obesity;
- osteoporosis;
- prenatal screening;
- prostate cancer;
- apnea syndrome;
- tobacco addiction.

Partial risk factors are preferably combined in a suitable weighted fashion to contribute to the integral risk factor for a certain disease computed for the subject under consideration. It will be appreciated that the partial risk factors together with respective computations may be different between the diseases. It will further be appreciated that partial risk factors are known per se, respective documents describing such partial risk factors are available. Although acquiring and processing of questions to the posed answers may be carried out manually, per specific selected disease, it is preferable to use a computerized algorithm for acquiring and processing data about the subject. The disease may be selectable from a user-accessible database of diseases. Further details of the method according to the invention will be discussed with reference to FIG. 1. In addition, it is possible that questions posed to the person comprise symptom-related questions. In this case the risk factor for acquiring a disease is determined based on the partial risk factors and further scores related to answers given to the symptom-related questions. Such scores related to symptoms are known for a suitable medical practitioner.

In a further embodiment of the method according to the invention, the method further comprises the steps of:
comparing the computed risk factor with a threshold value of the deterministically established risk factor of the disease;
informing the subject about an increased risk factor when the computed risk factor is at least equal to the said threshold value.

It is found to be advantageous to provide a direct and preferably real-time feed back of results of the determination of a risk factor for acquiring a certain disease. Although in most cases such feed-back may be provided to the individual being subjected to the questionnaire, it is also possible that such feed-back is provided to another person, for example a general practitioner, a health insurance authority, a supervisor, a parent or any other suitable person. This embodiment of the method according to the invention will be discussed in further detail with reference to FIG. 2.

In a further embodiment of the method according to the invention questions from the plurality of questions for different diseases are cross-linked.

It is found to be preferable, particularly for a computerized implementation of the method according to the invention, to cross-link identical questions forming part of respective questionnaires relevant for different diseases. For example, a question pertaining to gender, life, life style, like fitness activities, nutrition pattern, smoking and/or drinking habits may be relevant to a plurality of diseases. Therefore, particularly when the method according to the invention is used to assess risk factors for a plurality of diseases simultaneously, answers given to the questions relevant for different diseases and their respective partial risk factors may be used in different computational algorithms regarding different diseases. In this way the subject does not have to provide same answers for same questions regarding different diseases in question.

In a still further embodiment of the method according to the invention, a further question in said plurality of questions is selected from a database of relevant questions in dependence of an answer given by the subject for the at least one preceding question in said plurality of questions.

It is found to be advantageous to provide a self-learning and self-tuning questionnaire. For example, by using a question generator subroutine for a computerized implementation of the method according to the invention suitable logic and/or artificial intelligence may be used for modeling personal characteristics of the subject in question. For example, some behavioral patterns may be pre-stored and may be adjusted in real-time by generating suitable questions pertaining to relevant behavioral patterns. In particular, it may be advantageous to arrange the question generator subroutine to first assess a coarse data, like gender, age, weight, smoking and/or drinking habits, marital status, etc, after which to assess fine data, like dynamic information. For example, weight increment may be important within a certain period, frequency and intensity of smoking and/or drinking habits, sexual activity and/or a number of different partners per time period, etc. By using the question generator subroutine an individualized profile of the subject may be modeled wherein partial risk factors may be substituted by partial risk factors of a first and a second order. Due to this feature a determination of the risk factor for acquiring a certain disease may be performed with increased accuracy and reliability.

The aforementioned self-learning/tuning is carried out, in a disclosed embodiment, through the use of computer-executable instructions stored on a computer-readable medium of a computer system and executed by the computer system.

In a still further embodiment of the method according to the invention the method further comprises the steps of:
linking the disease from the database of diseases with tests;
feed-backing said tests to the subject for a disease with an increased risk factor.

It may be advantageous to provide medically justified advice to the subject regarding at least a minimum number of tests necessary for establishing whether a computed elevated risk for a specific disease have already led to acquiring such disease. In this case the tests relate to medical tests necessary for diagnosing a presence of a disease. For example, in cases when it is established that a person in question has an increased risk for colon cancer, a colonoscopy may be advised by the program. It will be appreciated that such advice may preferably be seen as a knowledge-based indicator for a purposeful selection of individuals forming a group within a population for which screening procedures have a positive effect. In addition, this has an advantage as an early diagnosis for a disease substantially increases a probability for cure. Alternatively, it is also possible that the tests relate to other types of tests, namely to tests arranged for investigating a presence of further partial risk factors related to the disease indicated with an increased risk factor. For example, in cases when it is established that the person in question has an increased risk for hart infarction, a lipid spectrum test to determine cholesterol level may be suggested. This is due to the fact than an increased cholesterol level increases a chance of a heart infarction on one hand, and can easily be treated on the other hand. Therefore, by discovering a number of patients' partial conditions contributing to the increased risk of a specific disease and by timely diagnosing and treating them, an overall risk for the disease may be successfully reduced. In addition the tests may relate to suitable diagnostic measures for investigating whether the person has a pre-stadium or an early stadium of a disease for which an increase risk factor is determined.

In a still further embodiment of the method according to the invention, the method comprises the steps of:

feeding-back results of diagnosis of a plurality of subjects for selective diseases to the database of deterministically established risk factors;

adjusting said deterministically established risk factor based on said feed-backing.

Again, the method is performed in large part by a computer system including a computer-readable medium that stores computer-executable instructions to facilitate carrying out the above-summarized method.

This particular embodiment has an advantage in that the background data, like risk factors and partial factors are subjected to fine tuning, for example based on matching between an incidence of individuals with increased risk factors for a certain disease and actual number of individuals for which the certain disease is diagnosed. In this way not only the risk factors and partial risk factors, but also threshold values for ruling an increased risk factor may be adjusted. It will be appreciated that such adjustment may lead to either an increase in respective values or a decrease in respective values.

It is found to be particularly advantageous to feed-back results of statistical analysis of subject's data pertaining to established diagnosis. For example, it may be preferable to first assess whether a deviation from an expected number of positive diagnoses does not deviate from a real number of positive diagnoses within a certain confidence interval. For the confidence interval, an interval of two or three standard deviations of a mean value may be selected. Additionally or alternatively, the group of subjects with increased risk factor may be subdivided into a suitable number of sub-groups, whereby the risk factors, partial risk factors and threshold values may be adjusted per sub-group. These measures may still further increase accuracy and reliability of the method according to the invention.

A computer program product according to the invention comprises instructions for causing a processor for carrying out the steps of the method as is set forth in the foregoing.

A computer system according to the invention comprises:
an input for selecting at least one disease;
an interface for interactively subjecting a subject to a plurality of questions relevant for the disease;
data acquisition means for acquiring respective answers from the subject to the said plurality of questions;
processing means and a computer-readable medium including computer-executable instructions for computing a risk factor for the subject for the at least one disease using said answers and an accessible database comprising a plurality of respective deterministically established partial risk factors for diseases, said partial risk factors being assigned to the said acquired answers.

The computer system including a computer-readable medium including computer-executable instructions according to the invention provides efficient, accurate and reliable means for determination of an increased risk factor of an individual for one or more diseases. Preferably, in the computer system according to the invention the computing means is arranged to process said plurality of questions for calculating respective risk factors for a plurality of diseases. It is found to be advantageous to provide a multi-tasking system wherein unique user data, like answers for the posed questions is used for computing potential elevated risk for acquiring a plurality of different diseases. Such system may provide a unique and efficient tool for patients, general practitioners and health insurance authorities. Based on educated, clinically justified advice about relevant diseases for a symptomless individual it is possible to rule out some of them by means of dedicated screening and to timely diagnose others which may increase success rate in therapy. As a cumulative result of such educated, clinically justified advice both health level of the population and screening cost-efficiency for the entire population may be increased.

In a further embodiment of the computer system according to the invention, the processing means including a computer-readable medium having computer-executable instructions is further arranged to:

feed-back results of diagnosis of a plurality of subjects for respective diseases to the database of deterministically established risk factors;

adjust said deterministically established risk factors based on said feed-backing.

The computer system according to the presently disclosed embodiment provides an intelligent self-adjusting tool for assessing clinically relevant data and for performing relevant follow-up and adjustment of deterministic factors, like risk factors, partial risk factors and threshold levels used for assessing health hazards of the population. It is noted that in a particular embodiment of the computer system according to the invention, wherein a suitable plurality of diseases is selected, a robust, time-efficient and clinically justified tool is provided for establishing whether a person in question has an elevated risk for acquiring one or more of the selected diseases.

These and other aspects of the invention will be discussed in further detail with reference to figures, wherein like reference numerals refer to like items. It will be appreciated that discussed embodiments are presented for illustrative purposes and may not be used to limit the scope of protection in any way.

DETAILED DESCRIPTION OF THE DRAWINGS

Figure 1:
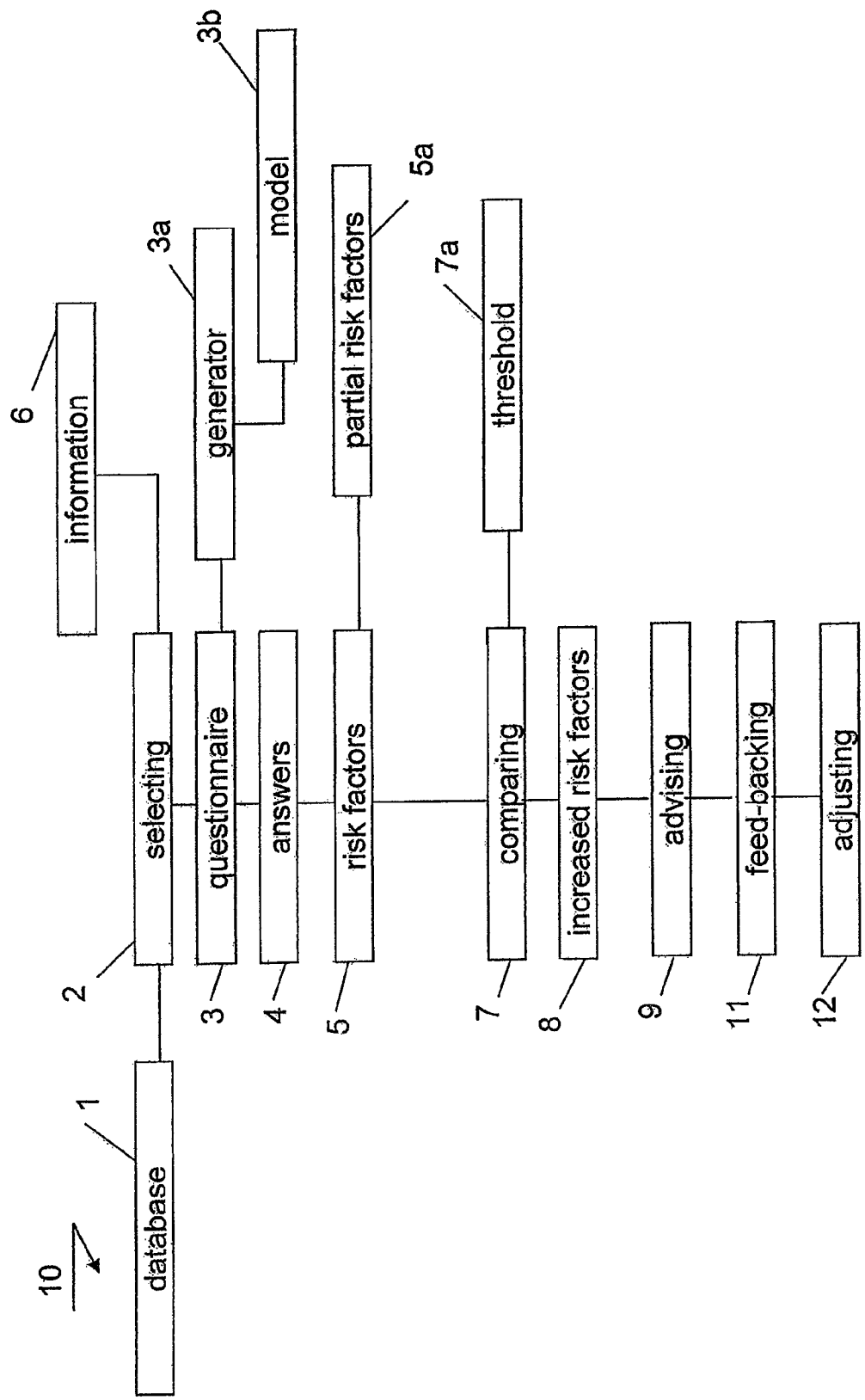
FIG. 1 presents a schematic view of an embodiment of a method according to the invention.

FIG. 1 presents a schematic view of the steps carried out by a programmed computer system including a computer-readable medium having computer-executable instructions for carrying out the summarized steps in an embodiment of a method according to the disclosure. The method 10 according to the disclosure may commence at the step 2 by selecting at least one disease from a database 1 of diseases. Alternatively, it is possible that all diseases from the database 1 are selected. Such selection may be performed by a user, or it may be a default selection provided by a suitable computer interface. It will be appreciated that the method according to alternative embodiments is not limited to computer implemented algorithms. In embodiments at least a part of the steps are carried out by a human operator. It is possible that a subject undergoes interaction with an operator of a suitable call center, a general practitioner, or any other suitable person capable of posing relevant questions from a questionnaire 3 and capable of acquiring answers 4 to these questions. It will be appreciated that a computerized implementation of the method according to the disclosure is preferable when a plurality of diseases are selected. It is possible that the method 10 according to the disclosure further comprises a step 6 of providing relevant clinical information of a course and symptoms of the selected disease or diseases. In this case the questions for the questionnaire 3 may be generated by a suitable question generation engine 3a which may cooperate with a suitable modeling routine or logic or an intelligence routine, all indicated by 3b, for building up subsequent questions, preferably in dependence on the provided answers 4 for the previous questions. After the answers 4 are acquired they are processed in relation to their respective partial risk factors 5a, after which an integral risk factor for acquiring the selected disease is computed/rendered by the programmed computer system. After this, at step 7 the computed risk factor is compared to a threshold value 7a, which may be pre-stored. In cases when it is established that the computed risk factor is at least equal the threshold value 7a a judgment about an increased risk factor 8 is undertaken which may be followed by putting forward an advice 9 regarding applicable screening. For illustrative purposes, some embodiments of respective subroutines related cerebro-vascular accident, cardiac malfunction and rectal cancer will be discussed.

Cerebro-Vascular Accident

One or more of the following sources may be used for establishing a threshold factor for evaluating whether a person in question has an elevated risk for acquiring cerebro-vascular accident:

Primary prevention and Health Services, STROKE 2007
Cijfers en feiten beroerte, Ned Hartstichting 2006
Primary prevention of ischemic stroke, STROKE 2006
Guidelines for prevention, STROKE 2006
Jaarbericht bevolkingsonderzoek, GR 2006
Transfusion Sickle Cell Stroke, NEJM 2005
Statins in stroke prevention, STROKE 2004
Screening CVA bij CABG, ICTVS 2004
Screening carotis interna, NTVG 2003
Improvements in treatments of CHD and stroke, STROKE 2003
Stroke prediction score, J Clin Epid 2002
A stroke prediction score in the elderly, J Clin Epid 2002
Carotid artery intima as a risk factor for stroke, NEJM 1999
Richtlijn beroerte CBO 1999
AHA/ACC scientific statement, J Am Col Cardiol 1999
AF and screening for stroke, J Med Screen 1998
Risk factors for ischemic stroke, STROKE 1998
Probability of stroke, STROKE 1991
Framingham Stroke Profile, STROKE 1991.

It will be appreciated that the presented list in neither compulsory, nor exhaustive. In particular, a per se known "Heart Study" study of Framingham investigated which risks males have for acquiring the cerebro-vascular accident. An abstract of the data presented in this study is given in Table 1. The respective risk factors are quoted for a time span of ten years.

TABLE 1

| Age | Risk over 10-years |
| --- | --- |
| 55-59 | 5.9% |
| 60-64 | 7.8% |
| 65-69 | 11.0% |
| 70-74 | 13.7% |
| 75-79 | 18.0% |
| 80-84 | 22.3% |

For example, a male of 62 years has a chance of 7.8% to acquire the cerebro-vascular accident within the next 10 years. Table 2 presents a plurality of partial risk factors contributing to the cumulative risk factor, as established in the Framingham study.

TABLE 2

| points | 0 | 1 | 2 | 3 | 4 | 5 | 6 | 7 | 8 | 9 | 10 |
| --- | --- | --- | --- | --- | --- | --- | --- | --- | --- | --- | --- |
| age | 55-56 | 57-59 | 60-62 | 63-65 | 66-68 | 68-71 | 72-74 | 75-77 | 78-80 | 81-83 | >83 |
| systolic blood pressure | 92-104 | 105-114 | 115-124 | 125-134 | 135-144 | 145-154 | 155-164 | 165-174 | 175-184 | 185-194 | >194 |
| clinically high RR | no | | yes | | | | | | | | |
| diabetes | no | | yes | | | | | | | | |
| smoker | no | | | yes | | | | | | | |
| cardiac dysfunction | no | | | yes | | | | | | | |
| LV-hypertrophy | no | | | | yes | | | | | | |
| dysfunction of the hart rythm | no | | | | | | | yes | | | |

From the analysis of Table 2, it follows that a man of 62 years of age having a systolic blood pressure of 160/90 mmHg, using medicine against hypertensia, having no diabetes or any cardiac history, however smoking, has a risk factor of 13 points. A conversion table from a point-oriented score to a 10-years deterministic probability of acquiring the cerebro-vascular accident is given in Table 3.

TABLE 3

| points | 10 year risk |
|--------|--------------|
| 1 | 2.6% |
| 3 | 3.5% |
| 5 | 4.7% |
| 7 | 6.3% |
| 9 | 8.4% |
| 11 | 11.2% |
| 13 | 14.8% |
| 15 | 19.5% |
| 17 | 25.5% |
| 19 | 32.9% |
| 21 | 41.7% |
| 23 | 51.8% |
| 25 | 62.8% |
| 27 | 83.7% |

From Table 3 it follows that an individual absolute risk of this 62-years of age male is 14.8% (instead of an averaged risk of 7.8% in accordance with Table 1). A relative risk (defined as a ratio of the individual absolute risk to an averaged risk) for this male is $R_r = 14.8\%/7.8\% = 1.9$. If, for example as a threshold value for an increased risk factor in accordance with the method of the invention, one has chosen an absolute risk factor of at least 10%, or a relative risk factor of at least 2, this male is indicated as having an increased risk for the cerebro-vascular accident. Therefore, it is important for a robust risk evaluating algorithm to use not only averaged risk factors, but also individually determined partial risk factors, said partial risk factors being dependent on certain anamnesis of this person. By letting the person in question answer specific general and disease-related questions, the partial risk factors are acquired, leading to a determination of the individual absolute risk and a computation of the relative risk factor.

For example, a list of questions may have a form of:
1. What is your gender? [male/female]
2. What is your age? [range 1, range 2, range 3, etc.]
   For a person younger than 54 years, or older than 86 years, for example, the module may stop as this individual is not expected to have an increased risk for acquiring cardiac malfunction based on deterministically established partial risk factors related to gender and age. For a person within 54 years and 86 years, the points are scored in accordance with a gender table, for example given in exemplary Table 4:

TABLE 4

| | 0 | 1 | 2 | 3 | 4 | 5 | 6 | 7 | 8 | 9 | 10 |
|---|---|---|---|---|---|---|---|---|---|---|---|
| Man | | | | | | | | | | | |
| age (yr) | 54-56 | 57-59 | 60-62 | 63-65 | 66-68 | 69-71 | 72-74 | 75-77 | 78-80 | 81-83 | 84-86 |
| Woman | | | | | | | | | | | |
| age (yr) | 54-56 | 57-59 | 60-62 | 63-65 | 66-68 | 69-71 | 72-74 | 75-77 | 78-80 | 81-83 | 84-86 |

3. Do you smoke? [yes/no]
   In dependence on affirmative or negative answer, partial risk factors are determined in dependence of the gender.
4. Have ever experienced the cerebro-vascular accident? [yes/no]
   If yes—end of module—the person in question has an elevated risk for acquiring a further cerebro-vascular accident.
5. Do you suffer from arterial disorders? [yes/no]
   When answered in the affirmative, the point score is increased accordingly, for a negative answer, the score is not changed.
6. Have you ever had a heart infarct? [yes/no]
   When answered in the affirmative, the point score is increased accordingly, for a negative answer, the score is not changed.
7. Have you ever suffered from a heart rhythm disorder? [yes/no]
   When answered in the affirmative, the point score is increased accordingly, for a negative answer, the score is not changed.
8. Have you suffered from arteries in lower extremities? [yes/no]
   When answered in the affirmative, the point score is increased accordingly, for a negative answer, the score is not changed.
9. Do you have diabetes? [yes/no]
   When answered in the affirmative, the point score is increased accordingly, for a negative answer, the score is not changed.

10. Do you have hypertensia? [yes/no]
   When answered in the affirmative, the point score is increased accordingly, for a negative answer, the score is not changed.
11. How high is your regular blood pressure? [mmHg/not known]
   The point score is increased in accordance with an exemplary embodiment, given in Table 5, dependent on gender. For 'not known', the point score is not changed.

TABLE 5

|  | 0 | 1 | 2 | 3 | 4 | 5 | 6 | 7 | 8 | 9 | 10 |
|---|---|---|---|---|---|---|---|---|---|---|---|
| Men |  |  |  |  |  |  |  |  |  |  |  |
| SBP (mmHg) | 99-105 | 106-116 | 117-126 | 127-137 | 138-148 | 149-159 | 160-170 | 171-181 | 182-191 | 192-202 | 203-213 |
| Women |  |  |  |  |  |  |  |  |  |  |  |
| SBP (mmHg) | 95-104 | 105-114 | 115-124 | 125-134 | 135-144 | 145-154 | 155-164 | 165-174 | 175-184 | 185-194 | 195-204 |

12. Do you use medicine against hypertension? [yes/no]
   For a negative answer, the point score is not changed, for an affirmative answer the point score may be increased by two points for men and for an affirmative answer for a female, the point score may be increased fine-tuned, for example in accordance with the exemplary embodiment, given in Table 6:

TABLE 6

| Women | 6 | 5 | 5 | 4 | 3 | 3 | 2 | 1 | 1 | 0 | 0 |
|---|---|---|---|---|---|---|---|---|---|---|---|
| SBP (mmHg) | 95-104 | 105-114 | 115-124 | 125-134 | 135-144 | 145-154 | 155-164 | 165-174 | 175-184 | 185-194 | 195-204 |

After completion of the questionnaire, which may comprise a more or less number of questions, as presented in the above exemplary embodiment, the total individual risk factor is computed based on the partial risk factors. Such computation may comprise an addition, or a weighted addition, in dependence on a significance of the specific item in the anamnesis for the integral individual risk factor. After the individual absolute risk factor is computed, a relative risk factor is computed, after which a decision is made regarding whether the person in question has an elevated risk factor for acquiring the cerebro-vascular accident.

In another example, the targeted potential disease may be a cardiac malfunction.

The questionnaire may be compiled by the question generator engine 3a of the programmed computer system as follows:

1. What is your gender? [male/female]
2. What is your age? [range 1, range 2, range 3]
   For a male younger than 50 years, the module may stop as this individual is not expected to have an increased risk for acquiring cardiac malfunction based on deterministically established partial risk factors related to gender and age. For a male older than 50 years, the question generator engine will proceed to question 3. For a female younger than 55 the module may stop as this female is not expected to have an increased risk for acquiring cardiac malfunction based on deterministically established partial risk factors related to gender and age. For a female older than 55 years the question generator engine will proceed to question 3.

It will be appreciated that the questions 1 and 2 are to be answered in case this subroutine is taken isolated. In case when the person in question selected a plurality of diseases for which the respective risk factors are to be determined, the general questions are to be used once, answers for them conceived to be used for different subroutines.

3. What is your weight?
4. What is your height?
   In cases when a computed Body Mass Index (BMI), expressed in $kg/m^2$ is less than 30, the questionnaire proceeds further with question 5. In case when BMI, expressed in $kg/m^2$ is at least equal than 30, the partial risk factor related to BMI is high, leading to a computation of an increased risk factor for cardiac dysfunction. In this case the individual may be advised to undergo specific screening program for establishing whether he or she suffers from cardiac dysfunction.
5. Do you smoke? [yes/no]
   When answered in the affirmative, the partial risk factor is elevated leading to an increased risk factor. Therefore, a screening test may be advised. Otherwise, the individual proceeds to question 6.
6. Have you smoked before? [yes/no]
   When a negative answer is provided, proceed with further questions. For a positive answer, the partial risk factor related to smoking habits is elevated leading to an increased risk factor. Therefore, a screening test may be advised.
7. How many cigarettes do you smoke a day? [range, for example 1-100 pieces]
   Calculation of pack-years, according to a formula ($P_y = N1/20 * N2$, wherein N1 is a number of cigarettes per day and N2 is a number of years the individual smokes).

An exemplary risk profile for a European citizen based on smoking profile is given in Table 7.

TABLE 7

10-year mortality rate

| systolic blood pressure | Females Nonsmoker | | | | | Females smoker | | | | | AGE | Males Nonsmoker | | | | | Males smoker | | | | |
|---|---|---|---|---|---|---|---|---|---|---|---|---|---|---|---|---|---|---|---|---|---|
| 180 | 8 | 10 | 11 | 13 | 14 | 15 | 18 | 20 | 23 | 26 | 65 | 13 | 15 | 17 | 20 | 22 | 23 | 27 | 31 | 35 | 38 |
| 160 | 8 | 7 | 8 | 9 | 10 | 11 | 13 | 15 | 17 | 19 | | 9 | 11 | 13 | 14 | 16 | 17 | 20 | 23 | 26 | 29 |
| 140 | 4 | 5 | 8 | 7 | 7 | 8 | 9 | 11 | 12 | 14 | | 6 | 8 | 9 | 10 | 12 | 12 | 15 | 17 | 19 | 21 |
| 120 | 3 | 3 | 4 | 5 | 5 | 5 | 7 | 8 | 9 | 10 | | 5 | 6 | 7 | 7 | 8 | 9 | 11 | 12 | 14 | 16 |
| 180 | 4 | 5 | 6 | 7 | 8 | 8 | 10 | 11 | 13 | 14 | 60 | 7 | 9 | 10 | 12 | 13 | 14 | 16 | 19 | 21 | 24 |
| 160 | 3 | 4 | 4 | 5 | 5 | 6 | 7 | 8 | 9 | 10 | | 5 | 6 | 7 | 8 | 9 | 10 | 12 | 14 | 16 | 17 |
| 140 | 2 | 3 | 3 | 3 | 4 | 4 | 5 | 6 | 7 | 7 | | 4 | 5 | 5 | 6 | 7 | 7 | 9 | 10 | 11 | 13 |
| 120 | 1 | 2 | 2 | 2 | 3 | 3 | 3 | 4 | 5 | 5 | | 3 | 3 | 4 | 4 | 5 | 5 | 6 | 7 | 8 | 9 |
| 180 | 2 | 3 | 3 | 4 | 4 | 4 | 5 | 6 | 7 | 8 | 55 | 4 | 5 | 6 | 7 | 8 | 8 | 10 | 11 | 13 | 15 |
| 160 | 2 | 2 | 2 | 3 | 3 | 3 | 4 | 4 | 5 | 5 | | 3 | 4 | 4 | 5 | 6 | 6 | 7 | 8 | 9 | 11 |
| 140 | 1 | 1 | 2 | 2 | 2 | 2 | 3 | 3 | 3 | 4 | | 2 | 3 | 3 | 4 | 4 | 4 | 5 | 6 | 7 | 8 |
| 120 | 1 | 1 | 1 | 1 | 1 | 1 | 2 | 2 | 2 | 3 | | 2 | 2 | 2 | 3 | 3 | 3 | 4 | 4 | 5 | 5 |
| 180 | 1 | 1 | 2 | 2 | 2 | 2 | 3 | 3 | 4 | 4 | 50 | 3 | 3 | 4 | 4 | 5 | 5 | 6 | 7 | | 9 |
| 160 | 1 | 1 | 1 | 1 | 2 | 2 | 2 | 2 | 3 | 3 | | 2 | 2 | 3 | 3 | 3 | 4 | 4 | 5 | 6 | 6 |
| 140 | 1 | 1 | 1 | 1 | 1 | 1 | 2 | 2 | 2 | 2 | | 1 | 2 | 2 | 2 | 2 | 3 | 3 | 4 | 4 | 5 |
| 120 | 0 | 1 | 1 | 1 | 1 | 1 | 1 | 1 | 1 | 2 | | 1 | 1 | 1 | 2 | 2 | 2 | 2 | 3 | 3 | 3 |
| 180 | 1 | 1 | 1 | 1 | 1 | 1 | 1 | 2 | 2 | 2 | 40 | 1 | 1 | 1 | 1 | 2 | 2 | 2 | 2 | 3 | 3 |
| 160 | 0 | 0 | 1 | 1 | 1 | 1 | 1 | 1 | 1 | 1 | | 1 | 1 | 1 | 1 | 1 | 1 | 2 | 2 | 2 | 2 |
| 140 | 0 | 0 | 0 | 0 | 1 | 1 | 1 | 1 | 1 | 1 | | 0 | 1 | 1 | 1 | 1 | 1 | 1 | 1 | 1 | 2 |
| 120 | 0 | 0 | 0 | 0 | 0 | 0 | 0 | 1 | 1 | 1 | | 0 | 0 | 0 | 1 | 1 | 1 | 1 | 1 | 1 | 1 |
| | 4 | 5 | 6 | 7 | 8 | 4 | 5 | 6 | 7 | 8 | | 4 | 5 | 6 | 7 | 8 | 4 | 5 | 6 | 7 | 8 | total cholesterol/HDL-cholesterol ratio

8. Do you suffer from coronary dysfunction or are you treated for such dysfunction? [yes/no/not aware]
   When answered no or not aware, question 9 is generated.
   When answered affirmatively, the partial risk factor is low, screening is not advised, end of module.
9. Have you ever had a stroke or a TIA? [yes/no/not aware]
   When answered no or not aware, question 10 is generated.
   When answered in the affirmative, screening test is not advised, end of module.
10. Do you suffer from arteries in legs? [yes/no/not aware]
    When answered no or not aware, question 11 is generated.
    When answered in the affirmative, a screening test is not advised, end of the module.
11. Do you suffer from diabetes? [yes/no/not aware]
    When answered no or not aware, question 12 is generated.
    When answered in the affirmative, a partial risk factor assigned to this answer is high leading to a computation of an increased risk factor, a screening test is advised, end of the module.
12. Do you suffer from hypertensia? [yes/no/not aware]
    When answered no or not aware, question 13 is generated.
    When answered in the affirmative, there is an elevated partial risk factor leading to an increased risk for acquiring the disease, a screening test is advised, end of the module.
13. Do you have an elevated cholesterol score? [yes/no/not aware]
    When answered no or not aware, question 14 is generated.
    When answered in the affirmative, there is an elevated partial risk factor leading to an increased risk for acquiring the disease, a screening test is advised, end of the module.
14. Do you have incidence of coronary dysfunction in the family? [yes/no/not aware]
    When answered no or not aware, a question related to, for example, a physical examination may be generated.
    When answered in the affirmative, an elevated partial risk factor is assigned and question 15 is generated.
15. Did any of your mother, father, brother or sister have any coronary or blood vessel dysfunction before age of 60? [yes/no/not aware]
    When answered no or not aware, question or questions related to use of medicaments may be generated.
    When answered in the affirmative, an elevated partial risk factor leading to an increased risk for acquiring the disease is assigned, a screening test is advised, end of the module.
16. Do you use any medicaments against hypertensia? [yes/no/not aware]
    When answered no or not aware, a question or questions related to general physical examination may be generated.
    When answered in the affirmative, an elevated partial risk factor leading to an increased risk for acquiring the disease is assigned, a screening test is advised, end of the module.

The presented questionnaire may be based on directives of:
i) Dutch Internists Society, "Richtlijnen cardiovasculair risicomanagement; 2004", which may be found on http://www.internisten.nl/files/crm.definitiefboekvorm (website).pdf
ii) Dutch Society of General Practitioners (NHG), "NHG0 Standaard Cardiovasculair risicomanagement. M84; 2007", which may be found on http://nhg.artsennet.nl/uri/?uri=ANGATE__6059__104_TICH_R183129611676033; and
iii) M. Naghavi et al "From Vulnerable Plaque to Vulnerable Patient—Part III: Executive Summary of the screening for Heart Attack Prevention and Education (SHAPE) Task Force Report", Am J. Cardiol.; 2006;
iv) Metabool syndroom, commentaar NTVG 2007;
v) Cardiovasculair risicomanagement, NHG 2007;
vi) Risk factors coronary heart disease, NHS 2006;
vii) Cardiovasculair risicomanagement, CBO 2006;
viii) Hart-en vaatziekten, Hartstichting 2006;
ix) SHAPE report, Am Journ Cardiol 2006;
x) Cardiovasculaire preventie, NVVC 2006;

xi) Richtlijnen cardiovasculair risicomanagement, NIV 2005;
xii) Sudden death in young athletes, NEJM 2003;
xiii) Heart failure nformation, NICE 2003.
xiv) Chronic heart failure, NICE 2003
xv) Third Joint Task Force, Eur Heart J 2003
xvi) The SCORE project. Eur Heart J 2003.

Other suitable sources of partial risk factors related to answers to the questions may be used. It is possible that different countries utilize slightly different partial risk factors and threshold values of the risk factor for acquiring of a disease. It is, therefore, possible that the method according to the disclosed embodiments, in particular a computerized method carried out by a programmed computer according to the disclosure herein comprises a preparatory step of geographical or ethnical identification, linked to a user-specific sub-database of partial risk factors and threshold values.

In cases where it is established that the individual undergoing interrogation by means of the questionnaire 3 has increased risk for acquiring a disease, for example a chance of at least 5% within ten years, he or she is provided with advice 9 related to a minimum number of screening tests necessary to diagnose a presence or absence of the disease.

For yet another disease, for example colon cancer, yet different literature sources are to be used wherein respective partial risk factors are presented. Such deterministically established partial risk factors may advantageously serve as a basis for formulating questions of the questionnaire in the method according to the disclosure. For example, the following publications may be used for determining the partial risk factors:

Screening for colorectal cancer using FOB, Cochrane 2007;
Immoraliteit coloncarcinoom screening, Medisch contact 2007;
Colonoscopy in Colorectal-Cancer Screening for Detection of Advanced Neoplasia, NEJM 2006;
Screening op darmkanker met sigmoïdoscopie of FOBT, Gezondheidsraad 2006;
Screenen op darmkanker via individuele risicoprofilelen, Gezondheidsraad 2006;
Bevolkingsonderzoek op colorectaal carcinoom, NTVG 2006;
Screening sigmoidoscopy and colonoscopy, Cochrane 2005;
Vormen van screening op darmkanker, Gezondheidsraad 2005;
Erfelijke tumoren: richtlijnen voor diagnostiek en preventie, STOET 2005;
Screening virtual colonoscopy, NEJM 2003;
Screening for colorectal cancer, AHRQ 2002;
Guidelines for colorectal cancer screening in high risk groups, GUT 2002;
Family history and risk of colorectal cancer, J Med Screen 2000;
The effect of fecal occult-blood screening on the incidence of colorectal cancer, NEJM 2000.

For example, for a person having a positive family anamnesis for the colon cancer, the risk factors may be as follows:

TABLE 8

Cumulative lifetime risk for colorectal carcinoma in dependence of family anamnesis

|  | Increase in risk | absolute risk |
|---|---|---|
| Negative family anamnesis |  | 4% |
| Sole 1st grade family member | 2× | 8% |
| sole 1st grade family member younger than 50 years | 4× | 16% |
| Two or more 1st grade family member | 4× | 16% |
| One 1st grade and one 2nd grade family member | 3× | 12% |

Based on the specific questionnaire targeting acquiring clinically relevant data on the person in question, the risk profile of this person is established based on the respective partial risk factors. Preferably, the partial risk factors are established in accordance with the above sources of literature. Table 9 presents a summary of averaged risk factors for acquiring colon cancer in dependence on the family anamnesis. It will be appreciated that these data represent summarized results of a profound European study on incidence of colon cancer (n=500.000) and may be used for setting suitable threshold values for judging whether person in question has an elevated risk for acquiring the colon cancer. For example, for less invasive screening methods, for example virtual colonoscopy, instead of actual colonoscopy, the threshold value of elevated risk may be set as low as 5% (instead of usually set value of 12%). In cases when the threshold value is set at 4%, men having no family anamnesis will be indicated for preventive screening. Therefore, the setting of the threshold value is a set-off between economical, medical and ethical arguments and no specific general value may be pointed out. Usually, the threshold value for judging upon an increased risk for colon cancer will be between 4% and 12% of the lifetime risk.

TABLE 9

Lifetime risk for acquiring colon cancer

|  | 0-34 jr | 35-39 jr | 40-44 jr | 45-49 jr | 50-54 jr | 55-59 jr | 60-64 jr | 65-69 jr | 70-74 jr |
|---|---|---|---|---|---|---|---|---|---|
| Men |  |  |  |  |  |  |  |  |  |
| negative family anamnesis | 0.0% | 0.1% | 0.1% | 0.3% | 0.5% | 0.9% | 1.7% | 2.7% | 4.5% |
| one $1^{st}$ grade family member <45 ys | 0.1% | 0.2% | 0.5% | 0.9% | 1.7% | 3.2% | 6.2% | 10.0% | 16.5% |
| one $1^{st}$ grad family member ≧45 ys | 0.0% | 0.1% | 0.2% | 0.4% | 0.8% | 1.5% | 2.9% | 4.7% | 7.7% |
| Two $1^{st}$ grade family members | 0.1% | 0.6% | 0.6% | 1.7% | 2.8% | 5.1% | 9.7% | 15.4% | 25.6% |

TABLE 9-continued

Lifetime risk for acquiring colon cancer

|  | 0-34 jr | 35-39 jr | 40-44 jr | 45-49 jr | 50-54 jr | 55-59 jr | 60-64 jr | 65-69 jr | 70-74 jr |
|---|---|---|---|---|---|---|---|---|---|
| one 1st grade family member with large adenoma | 0.1% | 0.1% | 0.2% | 0.5% | 0.8% | 1.4% | 3.2% | 5.1% | 8.4% |
| Women |  |  |  |  |  |  |  |  |  |
| negative family anamnesis | 0.0% | 0.1% | 0.1% | 0.2% | 0.4% | 0.7% | 1.1% | 1.7% | 2.5% |
| one 1st grade family member <45 ys | 0.1% | 0.2% | 0.4% | 0.8% | 1.5% | 2.5% | 4.1% | 6.1% | 9.2% |
| one 1st grad family member ≧45 ys | 0.0% | 0.1% | 0.2% | 0.4% | 0.7% | 1.2% | 1.9% | 2.8% | 4.3% |
| two 1st grade family members | 0.0% | 0.6% | 0.6% | 1.1% | 2.3% | 4.0% | 6.3% | 9.7% | 14.2% |
| one 1st grade family member with large adenoma | 0.1% | 0.1% | 0.2% | 0.4% | 0.7% | 1.3% | 2.1% | 3.1% | 4.7% |

Preferably, the method according to the disclosure further comprises the step of feed-backing 11 results of diagnosis of a plurality of subjects for respective one or more diseases to the database of deterministically established risk factors for purposes of adjusting 12 said deterministically established risk factors based on said adjusting. In such a way the method according to the disclosure is self-tuning, whereby respective risk factors, partial risk factors and threshold values are adjusted (decreased or increased) in dependence on, for example, a rate of positive diagnosis reports for a specific disease per group of subjects having elevated risk factor for acquiring such disease. It will be appreciated that such feature may lead to a further improvement of accuracy of the method according to the disclosure. Next to this, cost-effectiveness of a suitable national health management policy is improved.

Figure 2:
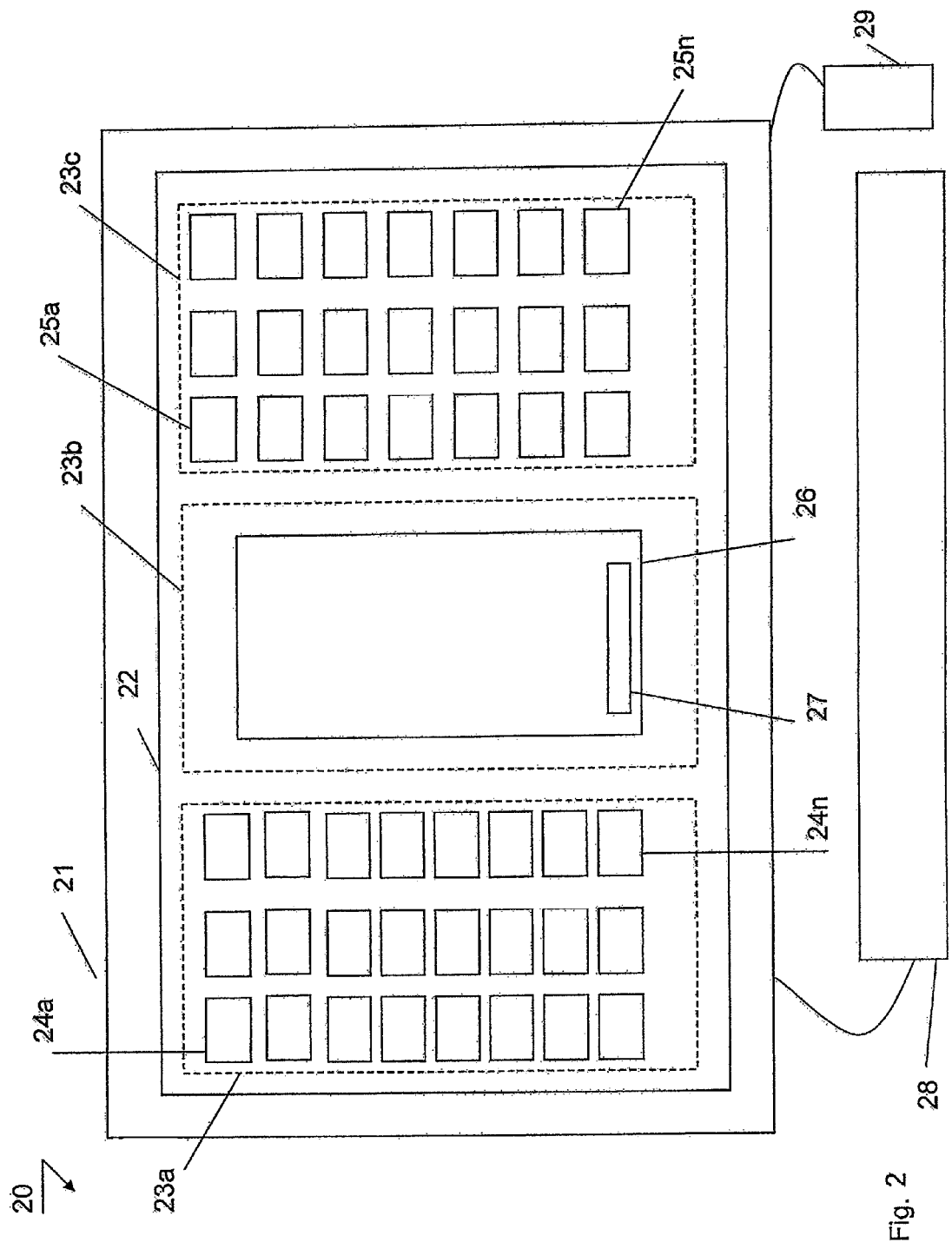
FIG. 2 presents a schematic view of an embodiment of a user interface of a computer system including a computer-readable medium storing computer-executable instructions for carrying out a computerized method according to the invention.

FIG. 2 presents a schematic view of an embodiment of a user interface of a computerized method according to the disclosure. As has been mentioned earlier, it is considered to be advantageous to implement the method according to the disclosure using an automated, preferably programmed computerized system. It will be appreciated that the terms 'computer' and 'computerized' refer not only to computers as known in the art, but also to any electronic device comprising a processor. For example, the method of the invention may be practiced on a mobile phone, personal organizer or any other suitable device capable of input/output and calculation operations.

In the present embodiment a user interface 20 is shown in combination with a display 21 of a computer, for example a remote computer which may be logged into a suitable server having a computer-readable medium and hosting a computer program product including computer-executable instructions for implementing the method according to the disclosure. In order to enable input/output operations the display may be controlled using suitable input/output devices like a keyboard 28 or a mouse 29. It will be appreciated that any other suitable means of data input is possible, including voice control interfaces.

In accordance with an aspect of the invention the user interface is arranged with a window 22 conceived to be provided on the display 21. The window 22 is divided into a suitable number of fields, like fields 23a, 23b, 23c. For example, the field 23a may be used to provide to the user a list of possible diseases for which it is possible to determine whether the user has an increased risk. Preferably, one or more diseases listed in the section "Summary of the invention" are presented. It is found to be convenient to provide an interactive list if diseases, whereby each disease corresponds to an actuatable button 24a, . . . , 24n. In cases where a user selects a disease the actuatable button may be arranged to automatically feed-back to the user a short description of the disease, its symptoms and any further relevant information.

Field 23c is preferably dedicated to a number of tests which may be recommended for a suitable screening procedure. Likewise, each individual test may be arranged on an actuatable button 25a, . . . 25n, which will feed-back relevant information about the test, like its scope and duration. Preferably, applicable tests are grouped in functional sections, pertaining to different type of tests. Such types may regard tests by means of a suitable interrogation, physical examination tests, laboratory tests, imaging procedures, specific tests related to measurement of a specific parameter or a value, specific consultative appointments with a medical specialist. As has been described earlier, each disease is linked to a screening program comprising one or more tests necessary for ruling whether the individual has a certain disease. It is possible that a particular test forms part of more than one screening program.

Field 23b may be arranged to provide an interactive window for the user for presenting questions and for acquiring answers. The questions are preferably generated by a question generation engine and are projected in the field 26. Preferably, such questions are formulated in a multiple choice format. Upon an event the user has entered an answer of his or her choice, he may actuate a button 27 to proceed further with the interactive field 23b. It will be appreciated that generation of the questions forming the questionnaire is carried out automatically, preferably based on the answers given by the user. The user may need to use the button or buttons 27 to scroll down the interactive window 26, or to choose another operating mode of the user interface 20.

Figure 3:
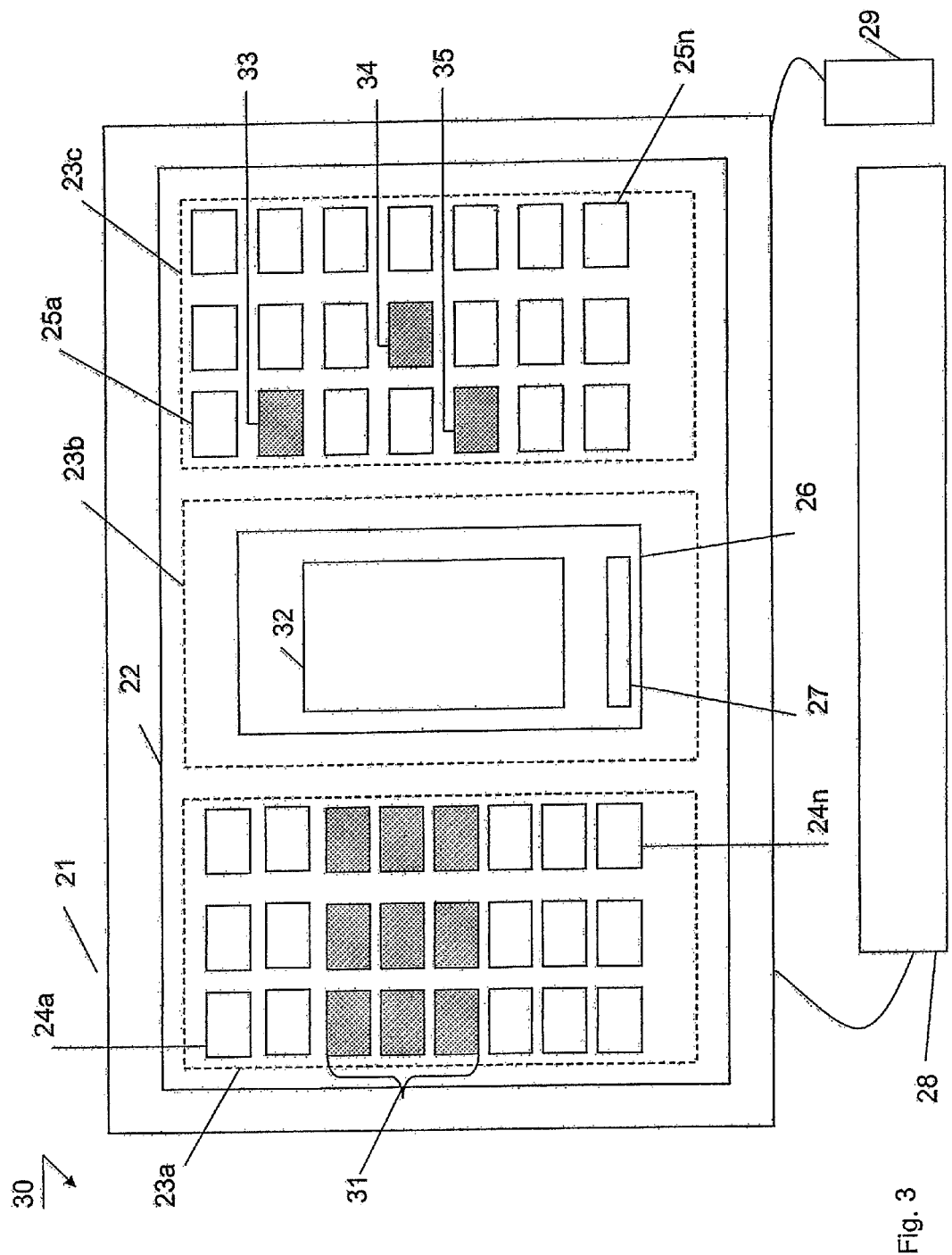
FIG. 3 presents a schematic view of an embodiment of a user interface after assertion of respective risk factors for a plurality of diseases.

FIG. 3 presents a schematic view of an embodiment of a user interface after assertion of respective risk factors for a plurality of diseases. The user interface 30 schematically illustrates a possible lay-out of the interactive screen 22 after the user has completed answering the questions from the questionnaire generated by a suitable question generating engine. It is seen that in the field 23a some actuatable buttons representing the diseases cumulatively indicated by 31 are highlighted. It will be appreciated that any form of highlighting may be selected for indicating to the user that for such specific diseases he or she has an increased risk factor. Also, some of the tests are highlighted. It will be understood that due to the fact that the tests are linked to a specific disease by means of an applicable clinically justified screening program, relevant tests may be highlighted only upon actuating a specific button representing a disease. Preferably, the test buttons 33, 34, are actuatable so that when the user clicks on any of the buttons, respective clinical information pertaining to the scope and the duration of suggested tests is fed-back. It is also possible that all actuatable buttons in the field 23a remain actuatable, so that the user is provided with a relevant substantiation why for certain highlighted diseases he or she has an increased risk factor and for non-highlighted diseases not. Additionally, in the informative field 23b it is possible to present suitable rationale for the user why it will be disadvantageous for his present health condition to undergo non-highlighted tests.

Preferably, the user interface 30 further comprises means for printing (not shown) the established individual profile of risk factors and/or sending it electronically to a further location. It is also possible that the profile is saved locally, for example when such interrogation is carried out in a practice of a general practitioner. By recursively subjecting an individual to such interrogations a dynamic study of his or her risk factors may be carried out further improving accuracy of determination of the individual risk factors.

Figure 4:
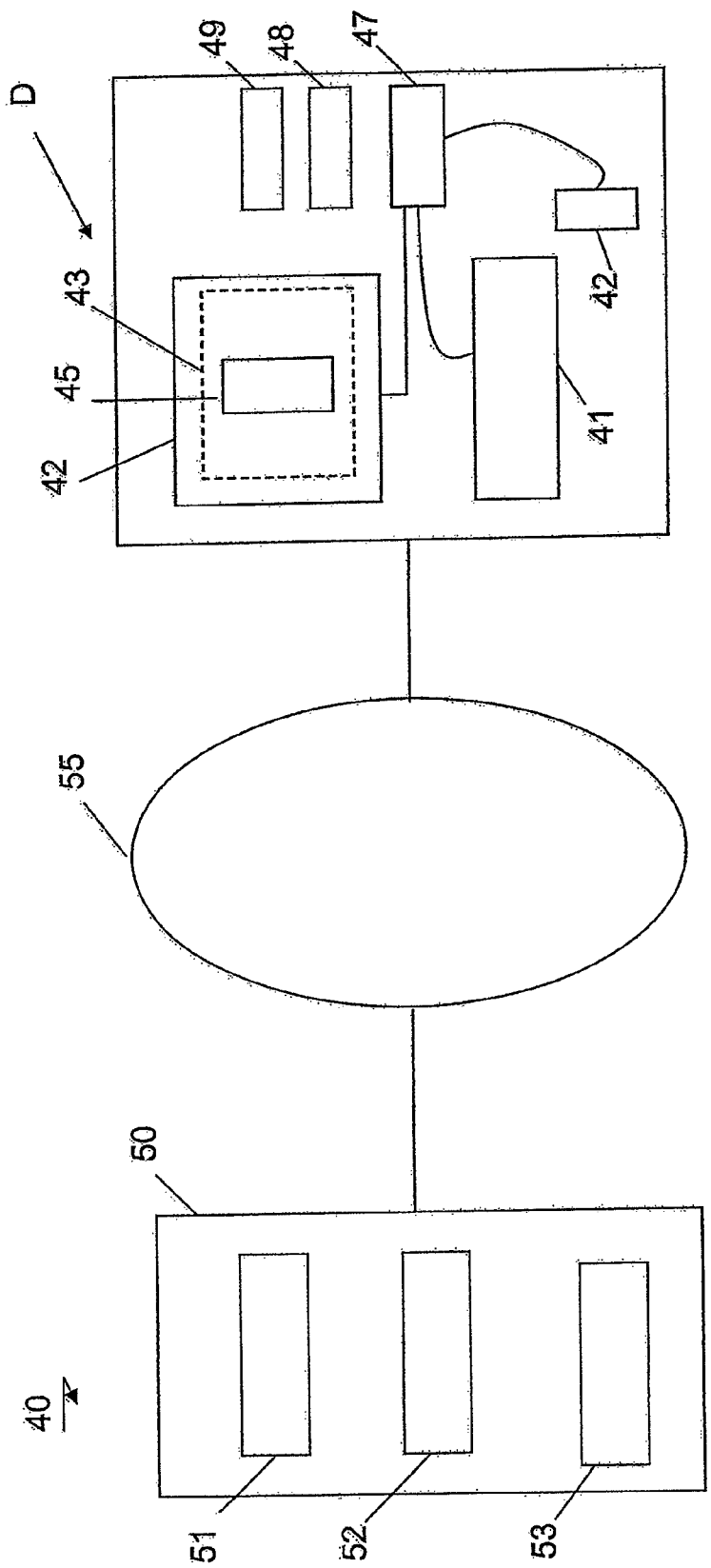
FIG. 4 presents a schematic view of an embodiment of a computer system according to the invention.

FIG. 4 presents a schematic view of an embodiment of a programmed computer system according to the disclosure. The computer system 40 may comprise a processor-based device D, whereby the processor 47 may relate to a full scale processor, for example of a personal computer or the like, or, alternatively, the processor 47 may relate to a microprocessor of a mobile device, like a mobile phone, an organizer on any other electronic apparatus capable of computing a risk factor for a subject for at least one disease using user-provided answers and an accessible database of deterministically established risk factor or risk factors for the disease, said risk factors or risk factors being related to said answers. The database 48 may be stored in a suitable format of a memory unit of the device D along with the computer program instructions for carrying out the disclosed method on a computer device D.

The computer system 40 according to the disclosure may further comprise a computer program product 49 on a computer-readable medium conceived to cause the processor 47 to carry out the steps of the method as is set forth with respect to the foregoing. For this purpose the computer program product 49 may be arranged to control a suitable user interface 43 conceived for enabling a user to select at least one disease to determine whether he or she has an increased risk for developing said disease. The computer program product 49 may be further arranged to control the interface 43 conceived to be displayed on a suitable display means 42 for interactively subjecting the user to a plurality of questions relevant for the said at least one disease. The computer program product 49 may be further arranged to control the user interface 43 to carry out acquisition of user's answers pursuant to the presented questions. Preferably, the computer program product 49 is arranged to provide the questions in a multiple choice format, so that no ambiguity may arise pursuant to interpretation of the user's answer and a partial risk factor related to said answer. In order to assist user in performing suitable input/output operations and for enabling user's interaction with the interface 43, the device D, for example a computer may be provided with input/output means, like a keyboard 41 or a mouse 42. It will be appreciated that other embodiments of the input/output means, like voice control, touchpad of a mobile electronic device, optical means or their equivalents are possible.

It will further be appreciated that it is not compulsory that all technical features of the computer system according to the disclosure are located in the same place. In the case of a telecommunication network or a computer network, it is possible that a remote host 50 is used for housing the processor 52, accessible database of deterministically established risk factors for diseases 53 and the computer program product 52. Preferably, the remote host is arranged to enable user interaction via a web page by means of a suitable internet or intranet means 55. This embodiment is advantageous in that a plurality of users may determine their respective risk factors for a disease or a plurality of diseases simultaneously.

It will be appreciated by those skilled in the art that while specific embodiments of the invention have been described above, that the invention may be practiced otherwise than as described. In addition, isolated features discussed with reference to different figures may be combined.

The invention claimed is:

1. A method of determining, with the use of a computer, whether a subject has an increased risk for acquiring a disease, said method comprising the steps of:
    selecting a plurality of diseases from a database of diseases accessible by the computer;
    interactively subjecting the subject to a plurality of questions relevant for the diseases using the computer;
    acquiring respective answers for the subject to the said plurality of questions, the computer being used to store the respective answers; and
    computing, using the computer, a risk factor for the subject for the diseases using said respective answers and an accessible further database comprising a plurality of respective deterministically established partial risk factors for the diseases, said partial risk factors being assigned to the respective answers by the computer.

2. The method according to claim 1, further comprising the steps of:
    comparing, for each of the diseases, the computed risk factor with a threshold value of the deterministically established risk factor for the disease using the computer; and
    informing the subject about having an increased risk factor when the computed risk factor is at least equal to the said threshold value.

3. The method according to claim 1, wherein questions of the respective plurality of questions for diseases are cross-linked.

4. The method according to claim 1, wherein a further question in said plurality of questions is selected, using the computer, from a database of relevant questions in dependence on an answer given by the subject for at least one preceding question in said plurality of questions.

5. The method according to claim 1, further comprising the steps of:
    linking the diseases from the database of diseases with tests;
    feeding-back said tests, by the computer, to the subject for a disease with an increased risk factor.

6. The method according to claim 1, further comprising the steps of:
    enabling a computer access for the subject to the database of diseases;
    enabling an interactive selection of the diseases from said database of diseases by the subject using a graphical user interface of the computer.

7. The method according to claim 1, further comprising the step of providing, by the computer, the subject with disease-related information for at least one selected disease.

8. The method according to claim 1, further comprising the steps of:
feeding-back, using the computer, results of diagnosis of a plurality of subjects for respective diseases to the database of deterministically established risk factors; and
adjusting, using the computer, said deterministically established risk factors based on said feeding-back.

9. The method according to claim 1, wherein said questions comprise symptom-related questions, said risk factor being determined based on said partial risk factors and further scores related to answers given to the symptom-related questions.

10. The method according to claim 8, wherein said feeding-backing comprises results of statistical analysis of subject's data in relation to established diagnosis.

11. The method according to claim 10, wherein said statistical analysis is performed for selected sub-groups of subjects within a group of subjects having an increased risk factor for a selected disease.

12. A non-transitory computer readable medium comprising computer-executable instructions for causing a processor for carrying out the steps:
selecting a plurality of diseases from a database of diseases accessible by the computer;
interactively subjecting the subject to a plurality of questions relevant for the diseases using the computer;
acquiring respective answers for the subject to the said plurality of questions, the computer being used to store the respective answers; and
computing, using the computer, a risk factor for the subject for the diseases using said respective answers and an accessible further database comprising a plurality of respective deterministically established partial risk factors for the diseases, said partial risk factors being assigned to the respective answers by the computer.

13. A computer system comprising:
an input for selecting a plurality of diseases;
an interface for interactively subjecting a subject to a plurality of questions relevant to the plurality of diseases;
a data acquisition interface for acquiring respective answers from the subject to the said plurality of questions;
a programmed processor including a computer-readable medium having computer executable instructions for computing a risk factor for the subject for the plurality of diseases using said answers and an accessible database comprising a plurality of respective deterministically established partial risk factors for diseases, said partial risk factors being assigned to the said acquired answers; and
a database comprising a plurality of respective deterministically established partial risk factors for diseases, said partial risk factors being assigned to the said acquired answers.

14. A computer system according to claim 13, wherein the programmed processor is further arranged for:
feeding-back results of diagnosis of a plurality of subjects for respective diseases to the database of deterministically established risk factors; and
adjusting said deterministically established risk factors based on said feeding-backing.

15. The computer system according to claim 13, wherein the programmed processor is further arranged for:
feeding-back results of diagnosis of a plurality of subjects for respective diseases to the database of deterministically established risk factors; and
adjusting said deterministically established risk factors based on said feeding-back.

* * * * *